United States Patent [19]

Croft

[11] Patent Number: 4,698,433

[45] Date of Patent: Oct. 6, 1987

[54] 2-METHYL-4-BENZYL-5-OXAZOLIDINONE

[75] Inventor: Alan P. Croft, Lake Jackson, Tex.

[73] Assignee: The Dow Chemical Company, Midland, Mich.

[21] Appl. No.: 827,854

[22] Filed: Feb. 10, 1986

[51] Int. Cl.[4] ........................................... C07D 263/08
[52] U.S. Cl. ..................................... 548/228; 562/433
[58] Field of Search ......................................... 548/228

[56] References Cited

U.S. PATENT DOCUMENTS 3,422,135 1/1969 Yamada et al. ...................... 548/228
3,856,854 12/1974 Schnettler et al. .................. 548/228

FOREIGN PATENT DOCUMENTS 2336718 6/1975 Fed. Rep. of Germany ...... 548/228
3084967 7/1978 Japan ................................... 548/228

OTHER PUBLICATIONS

Dane et al, CA 53-21695d.
Strukov, CA 50-4127d.
Shemyakin et al, CA 44-1096d.
Weygand et al, CA 06-115943q.
Strukov, CA 48-3962f.
Davidovich et al, CA 90-87335t.

Primary Examiner—Donald G. Daus
Assistant Examiner—Cecilia Shen
Attorney, Agent, or Firm—Gunn, Lee & Jackson

[57] ABSTRACT

This invention relates to a new composition of matter known as 2-Methyl-4-benzyl-5-oxazolidinone and a method of preparation of the new composition comprising combining ethyl acetate and the azlactone of α-acetoaminocinnamic acid in the presence of a catalyst such as W-2 Raney nickel. By using the new composition of matter of this invention the synthesis of L-phenylalanine is shortened to fewer reactions and process steps from the current lengthy, multistep means of synthesis.

2 Claims, No Drawings

2-METHYL-4-BENZYL-5-OXAZOLIDINONE

THE FIELD OF THE INVENTION

This invention relates to a new composition of matter known as 2-methyl-4-benzyl-5-oxazolidinone and a method of preparation of this new composition comprising combining ethyl acetate and azlactone of α-acetoaminocinnamic acid in the presence of a catalyst such as W-2 Raney nickel.

BACKGROUND OF THE INVENTION

L-phenylalanine is an essential amino acid. An amino acid is an organic acid containing both a basic amino group ($NH_2$) and an acidic carboxyl group (COOH). Amino acids are amphoteric, having the capacity to act as an acid or base, and exist in aqueous solution as dipolar ions. The amino acids that have been established as protein constituents are alpha-amino acids where the amino group is attached to the carbon atom next to the carboxyl group as in L-phenylalanine. Amino acids can be obtained by hydrolysis of a protein or synthesized in various ways such as by fermentation of glucose. An essential amino acid is one which cannot be synthesized by the human body and is necessary for survival, examples being isoleucine, phenylalanine, and others.

L-Phenylalanine is an important, essential amino acid used as a dietary supplement, in biochemical research, in synthetic sweeteners, and as a laboratory reagent. It is isolated commercially from proteins such as ovalbumin, lactalbumin, zern, and fibrin. The synthesis of L-phenylalanine is a lengthy multistep process. By using the new composition of matter of this invention, known as 2-methyl-4-benzyl-5-oxazolidinone, the synthesis of L-phenylalanine is shortened to fewer reactions and process steps. The cost of producing the valuable amino acid, L-phenylalanine, is thus reduced. In addition, the new compound could function as a suitable substrate for an enzymatic synthesis of L-phenylalanine.

DETAILED DESCRIPTION OF THE PREFERRED EMBODIMENT

L-phenylalanine is an important, essential amino acid which cannot be synthesized by the human body and is necessary for survival. Other uses for L-phenylalanine besides as a dietary supplement are in synthetic sweeteners, as a laboratory reagent, and in biochemical research. The commercial importance cannot be overstated. Currently the synthesis of L-phenylalanine is a high cost, lengthy multistep process. Synthesis steps can be eliminated and the process of making L-phenylalanine shortened and the cost reduced considerably by finding and utilizing raw materials already containing the necessary hydrocarbon groups which, by well known organic reactions, create the required end products for further synthesis. The new composition of matter of this invention, 2-Methyl-4-benzyl-5-oxazolidinone, allows such a shortening of the normal lengthy synthesis of L-phenylalanine thus also reducing the cost of the synthesis. 2-Methyl-4-benzyl-5-oxazolidinone contains the necessary phenyl and amino groups and when the heterocyclic ring is cleaved will also produce the required carboxyl group for synthesis of L-phenylalanine. The saturated heterocyclic ring of 2-Methyl-4-benzyl-5-oxazolidinone is broken in the synthesis of L-phenylalanine allowing the alkyl radical, $CH_3CH$, to leave while hydrogen attaches to the broken ends of the ring. In addition, the new compound could function as a suitable substrate for an enzymatic synthesis of L-phenylalanine.

The new composition of matter of this invention, 2-Methyl-4-benzyl-5-oxazolidinone, is prepared by the following novel and unobvious method of this invention. In a container such as a Parr bomb, a solvent such as ethyl acetate partially fills the container and the azlactone of α-acetoaminocinnamic acid and a catalyst such as a Raney nickel are added. While any Raney nickel can be used, the preferred catalyst is W-2 Raney nickel. Other Raney nickel are acceptable. This bomb is then pressurized with hydrogen after purging. An elevated temperature is maintained in the bomb for a set time period with stirring. After the set reaction period the bomb is depressurized, opened and the reaction mixture removed. This reaction mixture is then filtered to remove the spent catalyst while the solvent is removed by evaporation. The resulting product is recovered as an oil. Mass spectrum analysis of the product shows a compound consistent with the following structure:

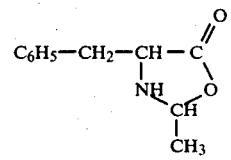

The temperature range for this preparation reaction is about 30° to about 150° C. Ideally, the process temperature is about 50° C. The pressure range for ths preparation reaction is between 100 and 1500 psi. Ideally, the pressure is maintained at about 600 psi. The elevated temperature and pressure are maintained several hours, preferably about 24 hours. Increased duration does not seem to enhance the conversion. The solvent is, in general terms, an organic solvent. The following examples are illustrative of specific embodiments of the invention.

EXAMPLE 1

300 ml of ethyl acetate as a solvent, 5.0 gm. of the azlactone of α-acetoaminocinnamic acid and 0.5 gm. of W-2 Raney nickel catalyst were placed in a 600 ml Parr bomb. The bomb was pressurized to 600 psi with hydrogen after purging. The bomb was then maintained at 50° C. for 24 hours with stirring. After the reaction period of 24 hours, the bomb was depressurized, opened, and the reaction mixture removed. The reaction mixture was filtered to remove the spent catalyst, and the solvent was removed by rotary evaporation. The resulting 4.5 gm. of product was recovered as an oil. A mass spectrum of the product was run which was consistent with the following structure:

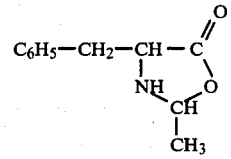

EXAMPLE 2

The new composition of this invention, 2-Methyl-4-benzyl-5-oxazolidinone, is used to shorten the synthesis of L-phenylalanine. The saturated heterocyclic ring of 2-Methyl-4-benzyl-5-oxazolidinone is cleaved, allowing the alkyl radical, CH₃CH, to leave while hydrogen attaches to the broken ends of the ring. The product recovered is L-phenylalanine.

While the foregoing is directed to a preferred embodiment of the present invention, other and further embodiments of the invention may be devised without departing from the basic scope thereof, and the scope thereof is determined by the claims which follow.

What is claimed is:

1. A composition of matter known as 2-Methyl-4-benzyl-5-oxazolidinone.

2. A composition of matter being:

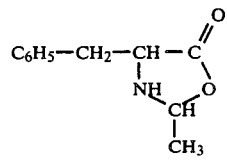

* * * * *